United States Patent
Tornay et al.

(10) Patent No.: US 10,001,478 B2
(45) Date of Patent: Jun. 19, 2018

(54) HETEROGENOUS SURFACE FUNCTIONALIZATION

(71) Applicant: MYCARTIS NV, Zwijnaarde / Ghent (BE)

(72) Inventors: Raphael Tornay, Illarsaz (CH); Patrick Van Den Bogaard, Morges (CH); Nicolas Demierre, Chatel-st-Denis (CH); Didier Falconnet, Vufflens-la-Ville (CH)

(73) Assignee: MYCARTIS NV, Zwijnaarde/Ghent (BE)

( * ) Notice: Subject to any disclaimer, the term of this patent is extended or adjusted under 35 U.S.C. 154(b) by 135 days.

(21) Appl. No.: 14/904,764

(22) PCT Filed: Aug. 14, 2014

(86) PCT No.: PCT/EP2014/067440
§ 371 (c)(1),
(2) Date: Jan. 13, 2016

(87) PCT Pub. No.: WO2015/024863
PCT Pub. Date: Feb. 26, 2015

(65) Prior Publication Data
US 2016/0153979 A1   Jun. 2, 2016

(30) Foreign Application Priority Data

Aug. 21, 2013   (EP) .................................. 13181142

(51) Int. Cl.
*G01N 21/75*   (2006.01)
*G01N 33/543*   (2006.01)
*B01L 3/00*   (2006.01)

(52) U.S. Cl.
CPC .. *G01N 33/54386* (2013.01); *B01L 3/502761* (2013.01); *B01J 2219/0056* (2013.01);
(Continued)

(58) Field of Classification Search
CPC .... B01J 2219/00693; B01J 2219/00725; B01J 2219/00536; B01J 2219/00637;
(Continued)

(56) References Cited

U.S. PATENT DOCUMENTS

| 2003/0198967 A1 | 10/2003 | Matson et al. | 435/6 |
| 2003/0211488 A1 | 11/2003 | Mirkin et al. | 435/6 |

(Continued)

FOREIGN PATENT DOCUMENTS

| EP | 2 484 447 | 8/2012 | ............... B01L 3/00 |
| WO | WO 01/53532 | 7/2001 | ............... C12Q 1/68 |

(Continued)

OTHER PUBLICATIONS

International Search Report from corresponding International Patent Application No. PCT/EP2014/067440, dated Oct. 11, 2014.

*Primary Examiner* — Dennis White
(74) *Attorney, Agent, or Firm* — Kusner & Jaffe

(57) ABSTRACT

The present invention relates to a microcarrier comprising at least a detection surface for performing an assay, said detection surface comprising a first area being functionalized with a first functional group for detecting at least a chemical and/or biological interaction, said first area being designed for providing a first signal. The microcarrier is characterized in that the detection surface further comprises a second area being designed for providing a second signal different from the first signal, said second signal being emitted during the assay. Thus, information about the presence of the at least a chemical and/or biological interaction is provided by a comparison of the first signal and the second signal.

14 Claims, 2 Drawing Sheets

(52) U.S. Cl.
CPC ............... *B01J 2219/0074* (2013.01); *B01J 2219/00536* (2013.01); *B01J 2219/00556* (2013.01); *B01J 2219/00612* (2013.01); *B01J 2219/00637* (2013.01); *B01J 2219/00693* (2013.01); *B01J 2219/00725* (2013.01); *B01L 2200/0647* (2013.01); *B01L 2300/021* (2013.01); *B01L 2300/0636* (2013.01); *B01L 2300/0819* (2013.01); *B01L 2300/0832* (2013.01)

(58) Field of Classification Search
CPC ...... B01J 2219/00612; B01J 2219/0056; B01J 2219/00556; B01J 2219/0074; B01L 2300/021; B01L 2200/0647; B01L 2300/0832; B01L 2300/0819; B01L 2300/0636; B01L 3/502761; G01N 33/54386
See application file for complete search history.

(56) References Cited

U.S. PATENT DOCUMENTS

| | | | |
|---|---|---|---|
| 2005/0079506 A1 | 4/2005 | Leon et al. | 435/6 |
| 2007/0048746 A1 | 3/2007 | Su et al. | 435/6 |
| 2007/0154895 A1 | 7/2007 | Spaid et al. | 435/6 |
| 2007/0248971 A1 | 10/2007 | Maerkl et al. | 435/6 |

FOREIGN PATENT DOCUMENTS

| | | | |
|---|---|---|---|
| WO | WO 02/052046 | 7/2002 | C12Q 1/68 |
| WO | WO 2004/027093 | 4/2004 | C12Q 1/68 |
| WO | WO 2004/047978 | 6/2004 | B01J 19/00 |
| WO | WO 2004/090168 | 10/2004 | C12Q 1/68 |
| WO | WO 2006/029234 | 3/2006 | G01N 33/543 |
| WO | WO 2006/037022 | 4/2006 | C12M 3/00 |
| WO | WO 2010/072011 | 7/2010 | B01L 3/00 |
| WO | WO 2012/106827 | 8/2012 | B01L 3/00 |

HETEROGENOUS SURFACE FUNCTIONALIZATION

FIELD OF THE INVENTION

The present invention relates to a microcarrier comprising a detection surface to detect at least a chemical and/or biological interaction. The present invention also relates to a method for performing a chemical and/or biological assay.

BACKGROUND OF THE INVENTION

The detection of chemical and/or biological interaction commonly involves microparticles equipped with a functionalized detection surface. When a solution contacts the detection surface, a target component comprised in the solution forms a chemical and/or biological interaction with a functional group grafted on the detection surface. Such interaction usually leads to the emission of a fluorescent signal indicative of the presence of the target component in the composition either directly if the target component is fluorescently labelled or indirectly if the interaction is revealed with a tertiary fluorescently labelled component.

However, non-specific and specific chemical and/or biological interactions may occur between the functionalized surface and components present in the solution, which are not the target component. For this reason, such detection assay often requires a control experiment to provide a control signal that ensures both the accuracy and the reliability of the results. Indeed, such control experiment typically allows determination of the background noise assimilated in that case to the control signal. As used herein, the term background noise is meant to define any non-specific interactions that occur when the functionalized surface is contacted with the solution comprising the target compound.

With the microparticles such as described in WO 2012/106827, a typical experiment protocol for detecting the target component involves two microparticles equipped with two different detection surfaces to provide two signals: a first microparticle is designed for detecting the specific and non-specific interactions of the targeted component to provide the fluorescent signal, without being able to distinguish both interactions, whereas a control microparticle is designed for detecting exclusively the background noise in order to provide the control signal. Thus, an approximation of the specific chemical and/or biological interaction between the target component and the detection surface can be deduced by a comparison of the fluorescent signal and the control signal.

Such experiment protocol is usable in order to analyse a solution with a homogeneous composition meaning that each microparticle is contacted with a predetermined and uniform environment. However, when the composition to be analysed is flowing in a microchannel comprising the microparticles, for example as described in WO 2010/072011, the protocol described above lacks of reproducibility. Indeed, when it comes to compare the signals emitted by two microparticles positioned in two different sections of said microchannel, each microparticle sees a different environment, especially when the concentration of target component is low and varies along and/or across the microchannel.

The present invention aims to remedy all or part of the disadvantages mentioned above.

SUMMARY OF THE INVENTION

The present invention fulfils these objectives by providing a microcarrier comprising at least a detection surface for performing an assay, said detection surface comprising a first area being functionalized with a first functional group for detecting at least a chemical and/or biological interaction, said first area being designed for providing a first signal, the microcarrier being characterized in that the detection surface further comprises a second area being designed for providing a second signal different from the first signal, said second signal being emitted during the assay, so that information about the presence of the at least a chemical and/or biological interaction is provided by a comparison of the first signal and the second signal.

The invention also relates to a method for detecting at least a chemical and/or biological interaction, the method comprising the successive steps of:
Providing a microcarrier according to the present invention;
Contacting said microcarrier with a composition designed for providing at least a chemical and/or biological interaction with the first area and/or the second area;
Measuring the first signal emitted by the first area and the second signal emitted by the second area;
Quantifying the presence of the at least a chemical and/or biological interaction on the first area by a differential analysis between the first signal and the second signal.

Thus, a microcarrier according to the present invention solves the problems mentioned above by providing a detection surface that further comprises a second area designed for emitting a second signal from a similar environment. The second area aims at providing complementary information about the chemical and/or biological interaction detected on the first area. A unique microcarrier according to the present invention provides two difference signals directly related to the composition of a solution that contacts the microcarrier. The two difference signals can be directly compared since they result from the same environment with regard to concentrations, especially when said concentration is dependent on the position in the microchannel. This was not possible with the microparticles of the prior art. Thus, the microcarrier according to the present invention offers a solution to the above mentioned issues regarding the detection of a target compound in a fluid flow and offers an increased reproducibility and an increased sensibility by taking into account the source of background noise.

According to an embodiment, the first area is at least partially distinct from the second area, preferentially the first area is distinct from the second area. This facilitates the comparison of the first signal with the second signal as the sources of emission of the two signals are at least partially physically separated.

In an embodiment, the first area and/or the second area are totally disconnected areas.

According to an embodiment, the first area and/or the second area are path-connected areas.

In an embodiment, the first area represents about 50% of the detection surface and/or the second area represents about 50% of the detection surface.

According to an embodiment, the first area and/or the second area comprise several path-connected subparts.

In an embodiment, the first area and the second area form together at least a checkerboard.

According to an embodiment, the first signal and the second signal are fluorescent signals.

In an embodiment, the first area and/or the second area comprise at least a metal. Indeed, methods of functionalization of metal-grafted surface are well described in the state of the art.

According to an embodiment, the first area comprises an antibody.

In an embodiment, the microcarrier has the shape of a wafer.

According to an embodiment, the first area and the second area are on the same side of the wafer.

In one embodiment of the present invention, the second signal is indicative of at least a specific chemical and/or biological interaction between said first functional group and a target molecule to be detected. Advantageously, the second signal is indicative of non-specific chemical and/or biological interactions between the second area and at least a molecule present in the assay.

In an embodiment, the microcarrier has the shape of a cylindrical wafer.

According to an embodiment, the chemical and/or biological interaction comprises the interaction of at least a target molecule comprised in a composition with the at least a first functional group.

In an embodiment, the first area is functionalized with the at least a first functional group for detecting the at least a target molecule comprised in the composition. The target molecule can be a biomolecule, for instance a protein or a nucleic acid.

According to an embodiment, the first signal is indicative of at least the chemical and/or biological interaction of the at least a target molecule with the first area.

In an embodiment the first signal is indicative of the specific chemical and/or biological interaction of the at least a target molecule with the first area together with the detection of the non-specific chemical and/or biological interaction of said target molecule with said first area.

According to an embodiment, the second area is functionalized for detecting the non-specific chemical and/or biological interaction of the at least a target molecule comprised in the composition.

In an embodiment, the microcarrier is designed to allow quantifying the specific chemical and/or biological interaction of the at least a target molecule comprised in the composition with that at least a first functional group.

According to an embodiment, the quantification of the specific chemical and/or biological interaction of the at least a target molecule comprised in the composition with that at least a first functional group is performed by a differential analysis between the first signal and the second signal.

In an embodiment, the microcarrier is encoded.

Advantageously, the encoded microcarrier of the invention further comprises a readable code. Thereby, the encoded microcarrier is encoded and functionalized in such a way that its functionalization is determinable by reading its code. A set of microcarrier is defined by one or more microcarriers encoded with the same code, said code corresponding to a particular first functional group on the first area, each set of microcarrier carrying a particular first functional group. When several sets of microcarriers are used, the first functional group of the first area of each set of the one or more microcarriers can be determined by reading the code of said microcarrier.

According to an embodiment, the first functional group is designed for recognizing the at least a target molecule comprised in a composition.

The invention also relates to a method for quantifying the specific chemical and/or biological interaction of at least a target molecule with the first area of the microcarrier according to the invention, said first area being functionalized with the at least a first functional group, the method comprising the steps of:

Providing at least a composition comprising the at least a target molecule;

Contacting said composition with at least a microcarrier according to the invention;

Measuring the first signal emitted by the first area and the second signal emitted by the second area;

Quantifying the specific interaction of the at least a target molecule on the first area by a differential analysis between the first signal and the second signal.

This method can also be used for quantifying the specific chemical and/or biological interaction of a plurality of target molecules with their corresponding first functional groups. To that end, a plurality of set of encoded microcarrier are used, each set of encoded microcarrier comprising at least a first functional group designed for recognizing a specific target molecule, wherein the first functional group of the first area of each microcarrier of a set is determined by reading the code of said encoded microcarrier.

In one embodiment, the first and the second signal are chosen amongst luminescence signals or chemi-luminescence signals.

In one embodiment, the first and/or the second area is engineered so as to permit surface enhanced fluorescence procedure.

The microcarrier according to the present invention or the method according to the present invention may be each embodiment disclosed in this application or be a combination of said embodiment.

BRIEF DESCRIPTION OF THE DRAWINGS

The present invention is further illustrated by the following detailed description set forth in view of the appended drawings, which represent an exemplary and explanatory embodiment of a microcarrier comprising a detection surface for performing an assay.

DETAILED DESCRIPTION OF THE INVENTION

Figure 1:
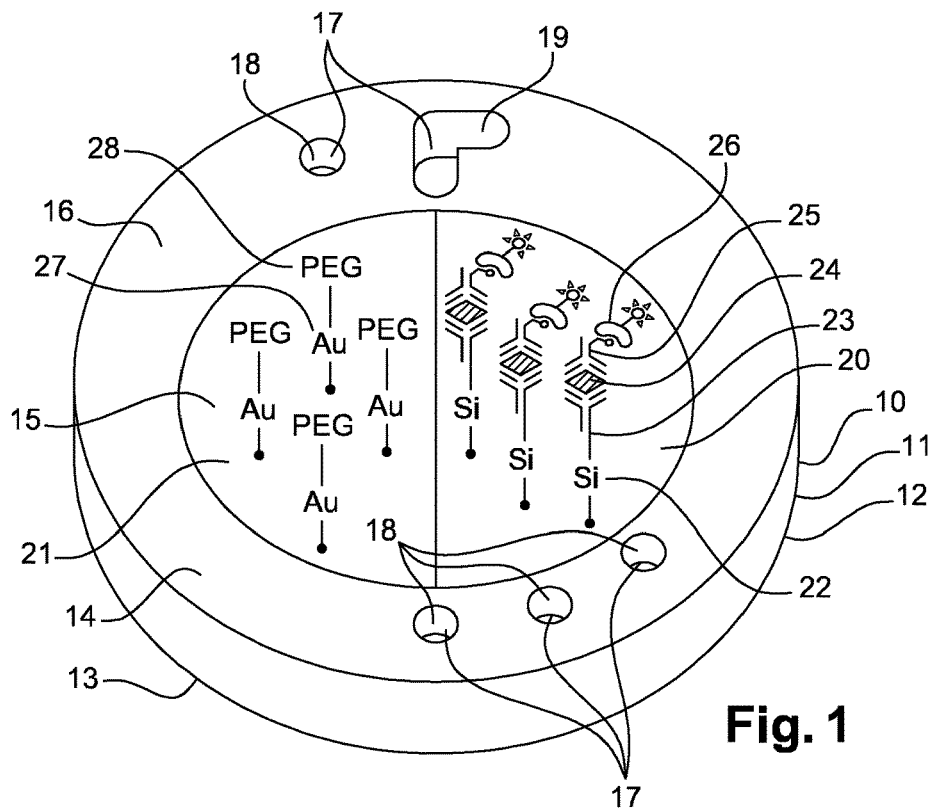
FIG. 1 is a view of a microcarrier according to a first embodiment comprising a detection surface divided in two areas.
Figure 3:
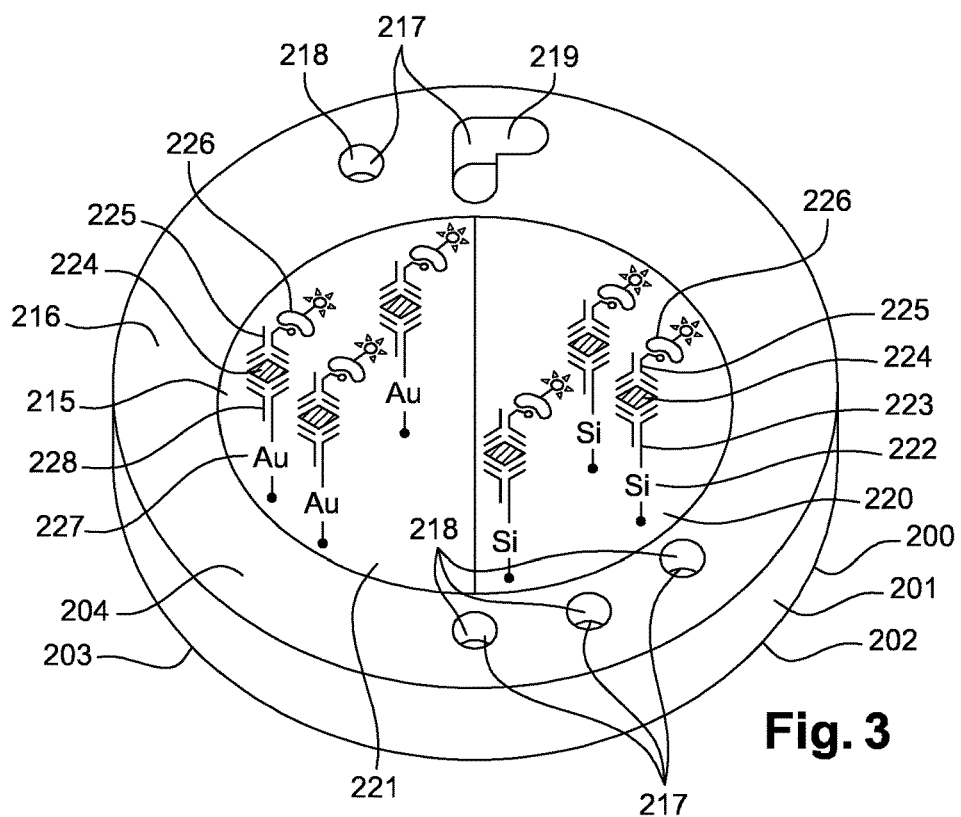
FIG. 3 is a view of a microcarrier according to a third embodiment comprising a detection surface with a first area and a second area designed for detecting an antigen.
Figure 2:
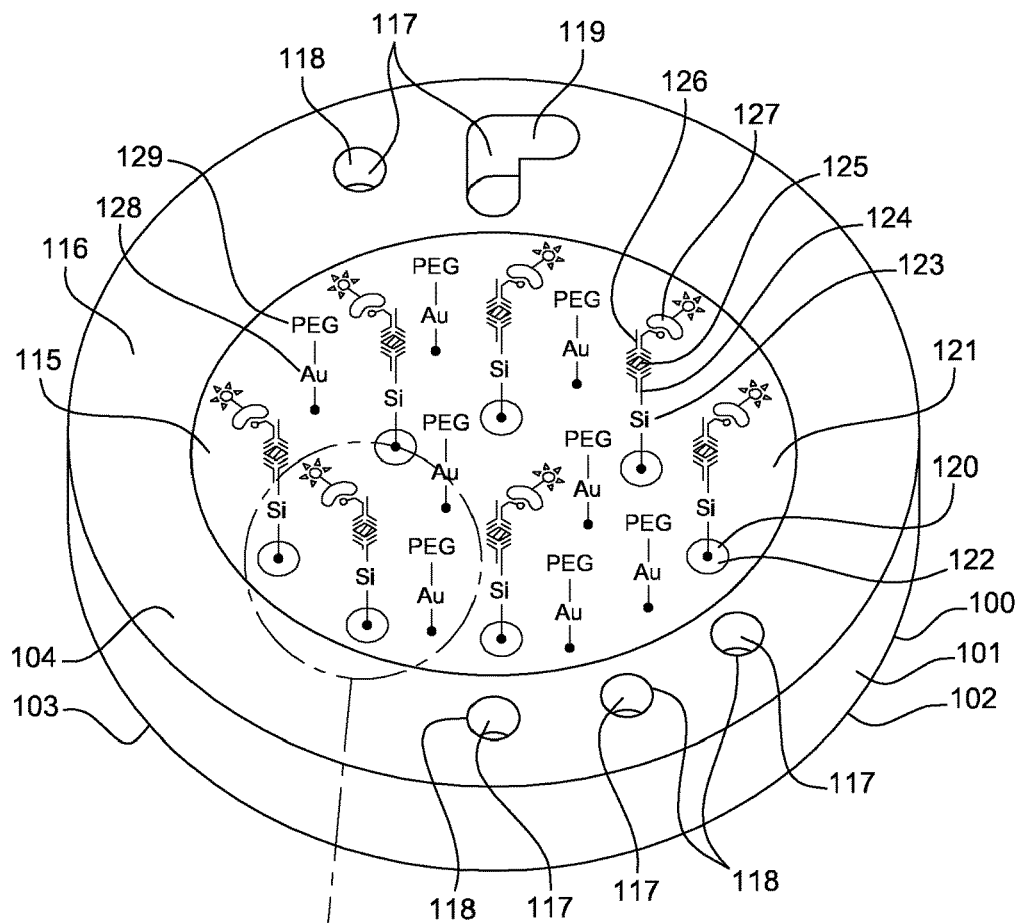
FIG. 2 is a view of a microcarrier according to a second embodiment comprising a detection surface with a first area divided in several subparts and a path-connected second area.
Figure 2:
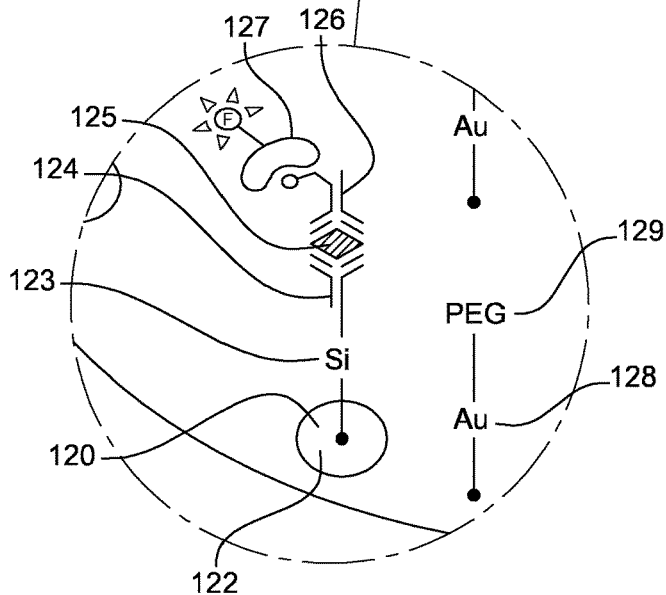

A microcarrier 10, 100, 200 according to the present invention comprises a body 11, 101, 201 having the shape of a cylindrical wafer being delineated by a cylinder surface 12, 102, 202 and two major surfaces 13, 14, 103, 104, 203, 204 as shown in FIGS. 1, 2 and 3, meaning that the height of the cylindrical wafer is notably smaller (by at least a factor two) than the radius of major surfaces 13, 14, 103, 104, 203, 204. In the embodiments represented in FIGS. 1 to 3, the wafer is a silicon wafer 16, 116, 216 covered with a native oxide layer. At least one of the major surfaces 14, 104, 204 comprises a detection surface 15, 115, 215 functionalized in order to detect at least a chemical and/or biological interaction. In the embodiments shown in FIGS. 1 to 3, the major surface 14, 104, 204 is functionalized in order to detect a target molecule comprised in a composition to be analysed and in said embodiments, the target molecule is an antigen 24, 124, 224. In the embodiments represented in FIGS. 1, 2, 3, the detection surface 15, 115, 215 are disk-shaped areas. The microcarrier 10, 100, 200 further comprises a readable code 17, 117, 217. Hence, a plurality of chemical and/or biological interaction can be detected by using a plurality of microcarriers 10, 100, 200, each microcarrier 10, 100, 200 being encoded with a unique readable code 17, 117, 217 corresponding to the functionalization of its detection surface 15, 115, 215. The readable code 17, 117, 217 comprises a distinctive pattern of a plurality of through holes 18, 118, 218. In the embodiments presented on FIGS. 1, 2 and 3, the readable code 17, 117, 217 is composed of four through holes. Such readable code 17, 117, 217 further preferably includes an asymmetric orientation mark 19, 119, 219 as an L-shaped hole, shown in FIGS. 1 to 3. The asymmetric orientation mark 19, 119, 219 is meant to distinguish the major surfaces 13, 14, 103, 104, 203, 204 from each other. The readable code 17, 117, 217 allows performing the detection and/or quantification of one or more target molecule comprised in a composition, each target molecule being detected and/or quantify by interacting with the detection surface 15, 115, 215 of a corresponding microcarrier 10, 100, 200.

The detection surface 15, 115, 215 comprises two distinct areas, a first area 20, 120, 220 and a second area 21, 121, 221. The first area 20, 120, 220 and the second area 21, 121, 221 are functionalized to provide respectively a first signal and a second signal. The functionalization of the first area 20, 120, 220 and/or the second area 21, 121, 221 can involve a metal. In the embodiments presented in FIGS. 1, 2 and 3 the first area 20, 120, 220 and the second area 21, 121, 221 are located on the same side of the silicon wafer 16, 116, 216. The embodiments represented in FIGS. 1 and 3 and the embodiment of FIG. 2 represent two different layouts of the first area 20, 120, 220 and of the second area 21, 121, 221 on the detection surface 15, 120, 220. In the first and third embodiments shown in FIGS. 1 and 3, the disk-shaped detection surface 15, 215 is divided into two semi-disk shaped areas which constitute two semi-disk-shaped areas, respectively the first area 20, 220 and the second area 21, 221. The first area 20 represents about 50% of the detection surface 15, 215 and the second area 21, 221 represents about 50% of the detection surface 15, 215. In such embodiments, the first area 20, 220 and the second area 21, 221 are both path-connected areas. In the second embodiment shown in FIG. 2, the first area 120 comprises a plurality of path-connected subparts 122 that form the first area 121. Each path-connected subpart 122 is, for example, a disk-shaped area.

The first area 20, 120, 220 is functionalized with spacers 22, 123, 222 as shown in FIGS. 1, 2, and 3. Such spacers 22, 123, 222 can be attached to the first area 20, 120, 220 using a well-known chemistry, implying for instance silanization of the surface silanol groups of the first area 20, 120, 220 of the silicon wafer 16, 116, 216 with a silicon derivative comprising a terminal silanol group at each end. The terminal silanol group resulting from the silanization is then submitted to an oxidation to convert the terminal silanol group into a carboxyl group. The resulting carboxyl groups are each covalently bound to a protein immunoglobulin G antibody (IgG) 23, 124, 223 using classic peptide bond chemistry. Thus, in the embodiments shown in FIGS. 1 to 3, the first functional group comprises the protein immunoglobulin G antibody (IgG) 23, 124, 223, said protein immunoglobulin G antibody (IgG) 23, 124, 223 being designed for recognizing the antigen 24, 124, 224.

When conducting an assay, the microcarrier 10, 100, 200 are placed in a microchannel. A solution comprising an antigen 24, 125, 224, a biotin-labelled antibody 25, 126, 225 and a fluorescent streptavidin 26, 127, 226 is flowed in the microchannel comprising the microcarrier 10, 100, 200. The protein immunoglobulin G antibodies (IgG) 23, 124, 223 are designed for interacting with the antigen 24, 125, 224. The biotin-labelled antibody 25, 126, 225 are designed to interact with the fluorescent streptavidin 26, 127, 226. During the assay, said antigen 24, 125, 224 are recognized by the biotin-labelled antibody 25, 126, 225 and interact with the fluorescent streptavidin 26, 127, 226 to provide the first signal indicative of at least the interaction of the antigen 24, 125, 224 with the IgG 23, 124, 223. Furthermore, in the embodiment shown in FIGS. 1 and 3, the antigen 24, 125 might also interact in a non-specifically manner via non-specific interactions with the first area 20, 120. In this case, the first signal is indicative of the specific interaction of the antigen 24, 125 with the IgG 23, 124 together with the non-specific interactions that might occur between said antigen 24, 125 and the first area 20, 120.

The second area 21, 121, 221 of the microcarrier 10, 100, 200 aims at providing the second signal, said second signal being different from the first signal. In the embodiments represented in FIGS. 1 and 2, the second area 21, 121 is used as an inner control that provides a background noise when the microcarrier 10, 100 is involved in an assay for detecting the antigen 24, 125. In such assay, the second area 21, 121 aims at evaluating the non-specific interactions that may occur between the target molecule of the composition and the detection surface 15, 215. To this end, the second area 21, 121 is functionalized with gold (Au) derivatives 27, 128 grafted with oligo- or poly(ethyleneglycol) units 28, 129 (PEG units 28, 129) using a thiol chemistry. The first signal provided by the first area 20, 120 can be corrected by taking into account the background noise measured by the second signal on the second area 21, 121 to evaluate the specific interaction of the antigen 24, 125 with the detection surface 15, 115.

In another embodiment shown in FIG. 3, the second area 221 is functionalized with gold derivatives 227 coupled to a second antibody 228, designed for also detecting the antigen 224. During the assay, said antigen 224 is recognized by the biotin-labelled antibody 225, said biotin-labelled antibody 225 being designed for interacting with the fluorescent streptavidin 226. Hence, a comparison between the first signal and the second signal allows the measurement of the affinity of antigen 224 with two different antibodies, the immunoglobulin G antibody (IgG) 223 and the second antibody 228 grafted on the detection surface 215 of the same microcarrier 200.

The invention also relates to a method for detecting at least a chemical and/or biological interaction. In the embodiments represented in FIGS. 1 and 2, the method is used to detect the antigen 24, 125. The method comprises the successive steps of:

Providing the microcarrier 10, 100 according to the present invention.

Contacting said microcarrier 10, 100 with the composition designed for providing the at least a chemical and/or biological interaction with the first area 20, 120 and/or the second area 21, 121.

Measuring the first signal emitted by the first area 20, 120 and the second signal emitted by the second area 21, 121. In the present case, the first signal and the second signal are fluorescent signals.

Quantifying the presence of the at least a chemical and/or biological interaction on the first area 121, 120 by a differential analysis between the first signal and the second signal. In the present case, the method permits to quantify the specific interaction of the antigen 24, 125 with protein immunoglobulin G antibody (IgG) 23, 124.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

Having described the invention, the following is claimed:

1. A microcarrier comprising:
    at least a detection surface for performing an assay of a composition flowing in a microchannel, said composition comprising at least one target molecule, wherein said detection surface comprises:
        a first area functionalized with a first functional group for providing a first signal indicative of (i) a specific chemical and/or biological interaction of the composition with the first area, together with (ii) a non-specific chemical and/or biological interaction of said composition with said first area,
            wherein the first area is functionalized with the first functional group for detecting said at least one target molecule of the composition, and
        a second area for providing a second signal different from the first signal, said second signal being emitted during the assay and being indicative of said non-specific chemical and/or biological interaction occurring in the first area,
            wherein the second area is functionalized for detecting the non-specific chemical and/or biological interaction between said at least one target molecule of the composition and the detection surface,
        wherein information about the presence of said specific chemical and/or biological interaction is provided by a comparison of the first signal and the second signal, and
        wherein the first signal and the second signal result from a same environment with regard to said composition, and are thereby directly comparable.

2. A microcarrier according to claim 1, wherein the first area is at least partially distinct from the second area.

3. A microcarrier according to claim 1, wherein the first area and/or the second area are totally disconnected areas.

4. A microcarrier according to claim 1, wherein the first area and/or the second area are path-connected areas.

5. A microcarrier according to claim 4, wherein the first area represents about 50% of the detection surface and/or the second area represents about 50% of the detection surface.

6. A microcarrier according to claim 1, wherein the first area and/or the second area comprise several path-connected subparts.

7. A microcarrier according to claim 6, wherein the first area and the second area form together at least a checkerboard.

8. A microcarrier according to claim 1, wherein the first signal and the second signal are fluorescent signals.

9. A microcarrier according to claim 1, wherein the first area and/or the second area comprise at least a metal.

10. A microcarrier according to claim 1, wherein the first area comprises an antibody.

11. A microcarrier according to claim 1, wherein the microcarrier has the shape of a wafer.

12. A microcarrier according to claim 11, wherein the first area and the second area are on the same side of the wafer.

13. A microcarrier according to claim 1, wherein the first area is distinct from the second area.

14. A method for detecting at least a chemical and/or biological interaction, the method comprising:
    providing a microcarrier comprising:
        at least a detection surface for performing an assay of a composition flowing in a microchannel, said composition comprising at least one target molecule, wherein said detection surface comprises:
            a first area functionalized with a first functional group for providing a first signal indicative of (i) a specific chemical and/or biological interaction of the composition with the first area, together with (ii) a non-specific chemical and/or biological interaction of said composition with said first area,
                wherein the first area is functionalized with the first functional group for detecting said at least one target molecule of the composition, and
            a second area providing a second signal different from the first signal, said second signal being emitted during the assay and being indicative of said non-specific chemical and/or biological interaction occurring in the first area,
                wherein the second area is functionalized for detecting the non-specific chemical and/or biological interaction between said at least one target molecule of the composition and the detection surface,
        wherein information about the presence of said specific chemical and/or biological interaction is provided by a comparison of the first signal and the second signal, and
        wherein the first signal and the second signal result from a same environment with regard to said composition, and are thereby directly comparable;
    contacting said microcarrier with a composition providing at least (i) a specific chemical and/or biological interaction and (ii) a non-specific chemical and/or biological interaction with the first area and (iii) said non-specific chemical and/or biological interaction with the second area;
    measuring the first signal emitted by the first area and the second signal emitted by the second area; and
    qualifying the presence of said specific chemical and/or biological interaction on the first area by a differential analysis between the first signal and the second signal.

* * * * *